US007201166B2

(12) United States Patent
Blaise et al.

(10) Patent No.: US 7,201,166 B2
(45) Date of Patent: Apr. 10, 2007

(54) INJECTION SYSTEM FOR DELIVERY OF A GASEOUS SUBSTANCE

(76) Inventors: Gilbert Blaise, 539 Stuart Street, Outremont, Québec (CA) H2V 3H1; Luc Dubé, 4036 Odélia, Laval, Québec (CA) H7R 5X4; Raymond Carrier, 3463 Ste-Famille, App. 1404, Montreal, Québec (CA) H2X 2K7

( * ) Notice: Subject to any disclaimer, the term of this patent is extended or adjusted under 35 U.S.C. 154(b) by 136 days.

(21) Appl. No.: 10/912,550

(22) Filed: Aug. 6, 2004

(65) Prior Publication Data

US 2005/0172966 A1    Aug. 11, 2005

(51) Int. Cl.
*A61M 15/00*    (2006.01)
(52) U.S. Cl. .............................. 128/203.12; 128/203.14
(58) Field of Classification Search ........... 128/203.12, 128/203.14, 204.21, 204.23
See application file for complete search history.

(56) References Cited

U.S. PATENT DOCUMENTS

| | | | |
|---|---|---|---|
| 4,204,536 A | 5/1980 | Albarda | |
| 4,681,099 A | 7/1987 | Sato et al. | |
| 4,686,975 A | 8/1987 | Naimon et al. | |
| 4,706,664 A | 11/1987 | Snook et al. | |
| 4,883,050 A | 11/1989 | Urman et al. | |
| 4,905,685 A | 3/1990 | Olsson et al. | |
| 4,932,401 A | 6/1990 | Perkins | |
| 5,074,299 A | 12/1991 | Dietz | |
| 5,237,990 A | 8/1993 | Psaros et al. | |
| 5,322,057 A | 6/1994 | Raabe et al. | |
| 5,385,940 A | 1/1995 | Moskowitz | |
| 5,395,612 A | 3/1995 | Griffith et al. | |
| 5,396,882 A | 3/1995 | Zapol | |
| 5,427,797 A | 6/1995 | Frostell et al. | |
| 5,485,827 A | 1/1996 | Zapol et al. | |
| 5,522,381 A * | 6/1996 | Olsson et al. ......... | 128/203.12 |
| 5,531,218 A * | 7/1996 | Krebs .................... | 128/203.12 |
| 5,558,083 A | 9/1996 | Bathe et al. | |
| 5,570,683 A | 11/1996 | Zapol | |
| 5,615,669 A * | 4/1997 | Olsson et al. ......... | 128/203.12 |
| 5,634,895 A | 6/1997 | Igo et al. | |

(Continued)

FOREIGN PATENT DOCUMENTS

CA    1255558    6/1989

(Continued)

OTHER PUBLICATIONS

Dubé, Luc et al. "Comparison of two administration techniques of inhaled nitrio oxide on nitrogen dioxide production". Canadian Journal of Anaesthesia, 1995. pp. 922-927.

*Primary Examiner*—Aaron J. Lewis
(74) *Attorney, Agent, or Firm*—Goudreau Gage Dubuc (57) ABSTRACT

An injection system for the delivery of a gaseous substance to a patient respiratory system is described herein. The injection system includes a control unit and a valve assembly including a valve and a valve actuator allowing partial opening of the valve and controlled by the control unit. The control unit is supplied with gas flow data and controls the valve assembly so that the opening of the valve is a function to the gas flow to thereby enable the control over the concentration of the gaseous substance delivered to the patient.

12 Claims, 9 Drawing Sheets

U.S. PATENT DOCUMENTS

| | | |
|---|---|---|
| 5,651,358 A | 7/1997 | Briend et al. |
| 5,732,693 A | 3/1998 | Bathe et al. |
| 5,839,433 A | 11/1998 | Higenbottam |
| 5,839,434 A | 11/1998 | Enterline |
| 5,845,633 A | 12/1998 | Psaros |
| 5,871,009 A | 2/1999 | Rydgren et al. |
| 6,016,801 A | 1/2000 | Philips |
| 6,032,667 A | 3/2000 | Heinonen |
| 6,125,846 A | 10/2000 | Bathe et al. |
| 6,155,256 A | 12/2000 | Wallin |
| 6,164,276 A | 12/2000 | Bathe et al. |
| 6,216,690 B1 | 4/2001 | Keitel et al. |
| 6,250,301 B1 | 6/2001 | Pate |

FOREIGN PATENT DOCUMENTS

| | | |
|---|---|---|
| CA | 1286943 | 7/1991 |
| CA | 1323284 | 10/1993 |
| CA | 2106969 | 3/1994 |
| CA | 2121384 | 10/1994 |
| CA | 2132268 | 5/1995 |
| CA | 2133516 | 5/1995 |
| EP | 0 659 445 A1 | 11/1994 |
| WO | WO 95/10173 | 10/1994 |
| WO | WO 96/11717 | 5/1995 |

* cited by examiner

INJECTION SYSTEM FOR DELIVERY OF A GASEOUS SUBSTANCE

FIELD OF THE INVENTION

The present invention relates to an injection system for delivery of a gaseous substance. More specifically, the present invention relates to an injection system for delivery of a gaseous substance to a patient, where the concentration of the gaseous substance delivered to the patient may be modified during the patient inspiratory phase and may be gradually modified over a predetermined number of patient inspiratory phases.

BACKGROUND OF THE INVENTION

It has been found that various chemical compounds, such as, for example, nitric oxide (NO), administered during a patient inspiratory phase may provide beneficial effects.

For example, NO presents some lung vasodilator properties that may be helpful for respiratory distress conditions such as respiratory distress syndrome of newborn.

Apparatus for delivering such gaseous chemical compounds have therefore been designed to deliver the compounds during the patient's inspiratory phase.

One such apparatus is described in Canadian Patent Application No. 2,106,696, filed on Sep. 22, 1993 and published on Mar. 25, 1994 and naming Robert Briand and Marie-Hélène Renaudin as inventors. In this document, Briand et al. describe an apparatus for delivering controlled doses of NO to the respiratory system of the patient without conventional pre-mixing of the NO with oxygen supplied by a ventilator device. The apparatus therefore includes means for detecting the beginning of a patient inspiratory phase and to open an electromagnetic valve for a predetermined duration to supply a controlled dose of NO. The duration and the pressure of the NO supplied dose is adjusted so as to obtain the desired NO concentration with respect to the average inhalation volume of the patient. The NO dose supplied is therefore not directly related to the inhalation volume of the patient. Of course, there is no NO injection during the expiration phase.

A major drawback of the apparatus described by Briand et al. is the automatic opening of the electromagnetic valve for a predetermined duration each time the beginning of an inhalation phase is detected. Indeed, if the patient repetitively draws short breaths, harm may be caused by the high concentration of NO injected to the patient.

In an article entitled: "Comparison of two administration techniques on inhaled nitric oxide on nitrogen dioxide production", published in Canadian journal of Anaesthesiology 1995, Vol. 42: 10, pages 922–927, Dubé et al. describe an injection system for delivering NO during inspiratory phase. In this injection system, an electronic circuit detects the beginning and the end of each inspiration by processing a flow signal supplied by a ventilator. At the beginning of the inspiratory phase, the electronic circuit opens a solenoid valve and NO is injected into the respiratory line. At the end of the inspiratory phase, the electronic circuit closes the solenoid valve and the injection of NO is stopped.

Figure 1:
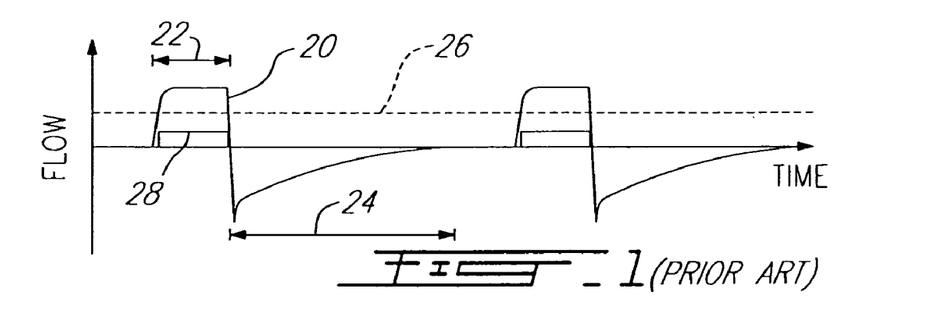
FIG. 1, which is labelled "PRIOR ART", illustrates a graph of flow vs time for a conventional ventilator when the ventilator is in a first mode.

FIG. 1 of the appended drawings is a graph of the inspiratory gas flow 20 vs time for a conventional ventilator when the ventilator is in a first mode. When it is in this mode, the flow of inspiratory gas is constantly delivered for a predetermined duration (inspiratory phase 22) and the patient then expires (expiratory phase 24). In the injection system proposed by Dubé et al., when the gas flow reaches a predetermined threshold level 26, a solenoid valve is open, delivering NO to the patient. The line 28 illustrates the injected flow of NO in the inspiration circuit over time. It is to be noted that the scale is different for the flow of inspiratory gas 20 and the flow 28 of NO. Indeed, line 28 illustrating the flow of NO is shown scaled up for illustrative purposes.

Figure 2:
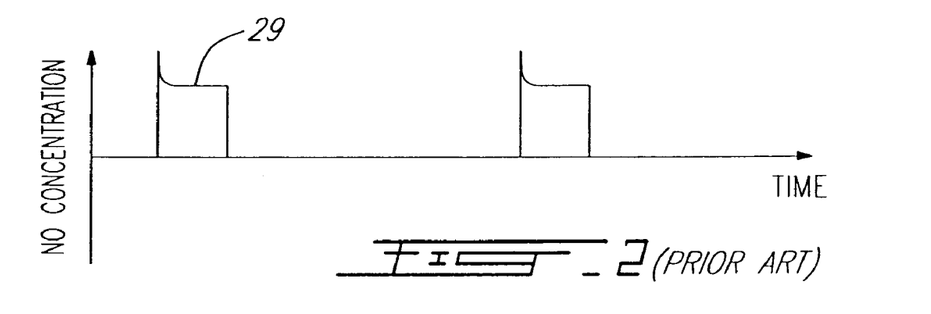
FIG. 2, which is labelled "PRIOR ART", illustrates a graph of nitric oxide concentration vs time corresponding to the graph of FIG. 1.

Since the solenoid valve used by Dubé et al. is of the type fully open/fully closed, the flow 28 of NO is constant when the valve is open. As can be seen from FIG. 2, the concentration 29 of NO is essentially constant over time during the inspiratory phases. When the inspiratory gas flow 20 falls below the threshold level 26, the solenoid valve is closed, stopping the flow of NO.

Figure 3:
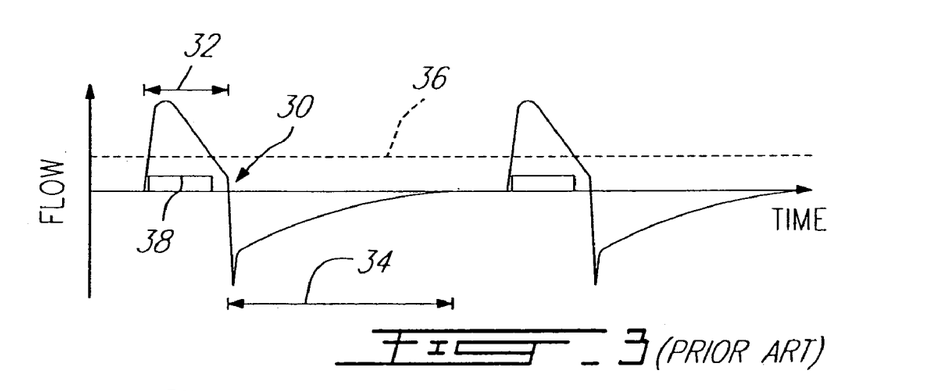
FIG. 3, which is labelled "PRIOR ART", illustrates a graph of flow vs time for a conventional ventilator when the ventilator is in a second mode.

FIG. 3 is a graph of the inspiratory gas flow 30 vs time for a conventional ventilator when the ventilator is in a second ventilating mode. When it is in this mode, the flow of gas is not constantly delivered for a predetermined duration but follows a particular curve during the inspiratory phase 32 and the patient then expires (expiratory phase 34). In the injection system proposed by Dubé et al., when the gas flow reaches a predetermined threshold level 36, the solenoid valve is open delivering NO to the patient. The line 38 illustrates the flow of NO over time. Again, it is to be noted that the scale is different for the flow of inspiratory gas and the flow 38 of NO. Indeed, line 38 illustrating the flow of NO is shown scaled up for illustrative purposes.

Figure 4:
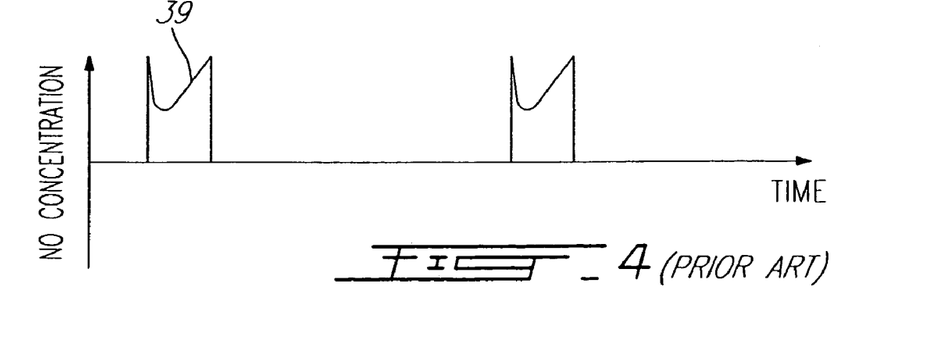
FIG. 4, which is labelled "PRIOR ART", illustrates a graph of nitric oxide concentration vs time corresponding to the graph of FIG. 3.

Since the solenoid valve used by Dubé et al. is of the type fully open/fully closed, the flow of NO is constant when the valve is open. As can be seen from FIG. 4, the concentration of NO (line 39) is not constant over time during the inspiratory phases but varies inversely with the flow of gas since the flow of NO is constant. When the inspiratory Gas flow 30 falls below the threshold level 36, the solenoid valve is closed.

A drawback of the injection system of Dubé et al. is that, in certain cases, the NO concentration is not constant during the inspiratory phase.

Canadian patent application No. 2,133,516 filed on Oct. $3^{rd}$, 1994 and naming Bathe et al. as inventors describes a nitric oxide (NO) delivery system monitoring the inspiratory gas flow of a patient and controlling a proportional valve to allow a calculated flow of NO to enter the inspiratory gas flow. The delivery system calculates the flow of NO in order to maintain a constant, user programmable, NO concentration in the inspiratory gas.

A drawback of the delivery system of Bathe et al. is that, while the delivery system may be programmed so that the concentration of NO in the inspiratory gas flow is constant, there are no provisions to modify the concentration of the NO during a particular inspiratory phase, or to program the variation of the concentration of NO over a number of successive inspiratory phases in view of gradually increasing or decreasing the concentration of NO supplied to the patient.

OBJECTS OF THE INVENTION

An object of the present invention is therefore to provide an improved apparatus for the delivery of gaseous substances.

SUMMARY OF THE INVENTION

More specifically, in accordance with the present invention, there is provided an injection system for the delivery of a gaseous substance from a container to a patient through a conduit coupled to the patient respiratory system; the injection system comprising:

a control unit controlling the injection system;

a valve assembly in connection with the conduit to selectively allow the delivery of the gaseous substance from the container to the conduit; the valve assembly including a valve and valve actuating means allowing variable opening of the valve; the valve actuating means being coupled to the control unit to be controlled thereby;

a flowmeter quantitatively measuring inspiratory gas flow in the conduit; the flowmeter being coupled to the control unit to supply inspiratory gas flow data thereto;

the control unit controlling the valve assembly so that the variable opening of the valve is responsive to the inspiratory gas flow in the conduit.

According to another aspect of the present invention, there is provided an injection system for the delivery of a gaseous substance from a container to a patient through a conduit coupled to the patient respiratory system; the respiratory system of the patient being also coupled to a ventilator forcing inspiratory gas therein; the injection system comprising:

a control unit controlling the injection system; the control unit receiving inspiratory gas flow data from the ventilator;

a valve assembly in connection with the conduit to selectively allow the delivery of the gaseous substance from the container to the conduit; the valve assembly including a valve and valve actuating means allowing variable opening of the valve; the valve actuating means being coupled to the control unit to be controlled thereby;

the control unit controlling the valve assembly so that the variable opening of the valve is responsive to the inspiratory gas flow supplied to the patient.

A major advantage of the present invention concerns the variable opening of the valve to increase or decrease the quantity of the gaseous substance delivered to the patient. Hence, it is possible to control the opening of the valve so that the variable opening of the valve is responsive to the inspiratory gas flow directed towards the respiratory system of the patient and thereby controlling the concentration of the gaseous substance delivered to the patient.

Other objects, advantages and features of the present invention will become more apparent upon reading of the following non restrictive description of preferred embodiments thereof, given by way of example only with reference to the accompanying drawings.

The subject of the present invention was developed at "Le Département de physique biomédicale, Pavillon Notre-Dame, Centre hospitalier de l'Université de Montréal (CHUM)"

DESCRIPTION OF THE PREFERRED EMBODIMENT

Figure 5:
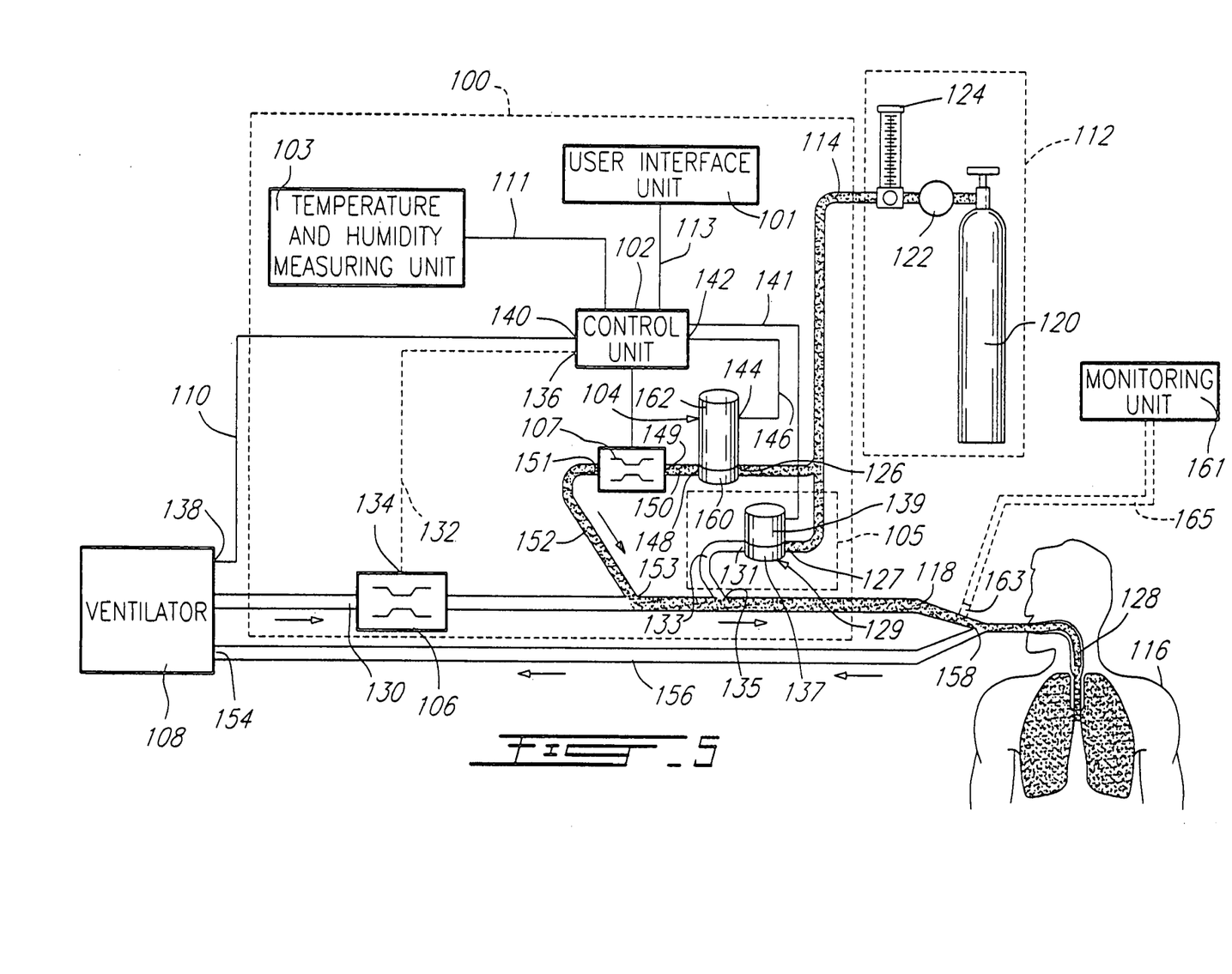
FIG. 5 schematically illustrates an injection system according to an embodiment of the present invention, the injection system being installed to a conventional ventilator.

FIG. 5 of the appended drawings illustrates an injection system 100 according to an embodiment of the present invention. The injection system 100 includes a user interface unit 101, a control unit 102, a temperature and humidity measuring unit 103, a valve assembly 104 a backup unit 105 an inspiratory gas flowmeter 106 and a gaseous substance flowmeter 107.

The injection system 100 is illustrated in FIG. 5 as being connected to a conventional ventilator 108 through a data cable 110, to a source of a gaseous substance 112 through a conduit 114 and to a patient 116 through an inspiratory conduit 118.

It is to be noted that the following description of the injection system 100 will be given with the particular example of nitric oxide (NO) injection, but that the system 100 could be used to inject other gaseous substance in the respiratory system of a patient.

The source of gaseous substance (NO) 112 includes a NO container 120, a pressure reducer 122 connected to the container 120 and a precision flowmeter 124 adjusting the maximum flow rate of NO in the injection system 100 and connected to the pressure reducer 122. The conduit 114 pneumatically connects the precision flowmeter 124 to a fluid input 126 of the valve assembly 104 and to a fluid input 127 of a backup valve assembly 129 of the backup unit 105 as will be described hereinafter.

The ventilator 108, when in operation, repetitively supplies a predetermined quantity of inspiratory gas to the respiratory system of the patient 116 through the inspiratory conduit 118 connected to an endotracheal tube 128.

The inspiratory gas supplied to the patient goes through the flowmeter 106, via conduit 130, thereby enabling the flowmeter 106 to measure the inspiratory gas flow supplied to the patient 116. Inspiratory gas flow data is supplied to the control unit 102 via a data cable 132, interconnecting an inspiratory gas flow data output 134 of the flowmeter 106 and an inspiratory gas flow data input 136 of the control unit 102. Of course, the inspiratory gas flow data is either in analog or in digital format, compatible with the control unit 102.

The data cable 132 is illustrated in dashed line in FIG. 5 since the data cable 132, along with the flowmeter 106, are not essential to the operation of the injection system 100 when the injection system 100 is connected to a conventional ventilator 108 provided with a flow data output. Indeed, the ventilator 108 includes an inspiratory gas flow data output 138 electrically connected to an inspiratory gas flow data input 140 of the control unit 102 through the data cable 110. The control unit 102 is therefore supplied with inspiratory gas flow data from either the independent flowmeter 106 or the data flow output 138 of the ventilator 108.

The control unit 102 includes a control output 142 electrically connected to a control input 144 of the valve assembly 104 via a control cable 146. The control unit 102 therefore controls the variable opening of the valve assembly 104. The valve assembly 104 may be a normally closed valve assembly or a normally open valve assembly but is advantageously a normally closed valve assembly for safety reasons. Indeed, it is advantageous that the valve automatically closes upon loss of electrical power.

The valve assembly 104 also includes a fluid output 148 pneumatically connected a fluid input 149 of the gaseous substance flowmeter 107 through a conduit 150. The flowmeter 107 includes a fluid output 151 connected to conduit 118 through a conduit 152 and a "Y" junction 153.

As can be seen from FIG. 5, the ventilator 108 also includes an expiratory gas inlet 154 connected to the conduit 118 through a conduit 156 and a "Y" junction 158. The patient's expiration gases is therefore returned to the ventilator 108.

The temperature and humidity measuring unit is provided with conventional means to measure relative humidity and temperature and to supply this data to the control unit 102 via a data cable 111. The measure of both humidity and temperature will enable the control unit 102 to determine the precise flow of the inspiratory gas and subsequently adjust the flow of NO.

The user interface unit 101 is connected to the control unit 102 via a data cable 113 enabling the user interface unit 101 to supply data pertaining to user's inputs to the control unit 102 and enabling the control unit 102 to supply data pertaining to information to be displayed on a display portion (not shown) of the user interface unit 101. For example, the user interface unit 101 includes controls operable by the user to determine the desired concentration of NO to be injected, the type of injection (constant or according to a predetermined pattern) and the variation of the NO concentration over time. These two controls will be further described hereinafter.

The display portion (not shown) of the user interface unit 101 can be used to display the following information:
the total amount of NO injected to the patient (mole);
the concentration of inspiratory $NO/NO_2$ (calculated) (ppm);
the decrease of $FiO_2$ following the NO injection (%); the flow of NO (cc/min);
the quantity of NO remaining in the container 120 (litres);
the NO flow curve; and
the ventilation flow curve.

It is believed within the skills of one of ordinary skills in the art to design the control unit 102 as to calculate or to obtain the above-mentioned quantities and concentration from the flowmeters and some initial data, and to format them to be displayed on a conventional display device. Or course, other data, such as, for example, the oxygen concentration supplied by the ventilator, is advantageously supplied to the control unit 102 to enable the determination of the $FiO_2$. It is also to be noted that models predicting the $NO_2$ concentration exist and are believed sufficient for the present purpose.

The valve assembly 104 includes a valve portion 160 including the fluid input 126 and output 148 and a valve actuating portion 162 including the control input 144. The valve actuating portion 162 advantageously transduces an electric signal supplied to the control input 144 to a mechanical opening of the valve portion 160.

As mentioned hereinabove, the injection system 100 includes a backup unit 105 intended to be automatically activated should problems occur with the injection system 100. Indeed, since NO is a drug, the abrupt stopping of the injection of NO could be armful to a patient. The backup unit 105 is thus provided with a backup valve assembly 129 having a valve portion 137 including the fluid input 127 and a fluid output 131 connected to the conduit 118 via a conduit 133 and a "Y" junction 135. The backup valve assembly 129 also includes a valve actuating portion 139 connected to the control unit 102 via a data cable 141 to monitor the status of operation of the control unit 102. The flow of NO through the valve portion 137, when it is open, is manually adjustable by the user. Therefore, the valve portion 137 automatically supplies a predetermined flow of NO should the injection system 100 fail. It is to be noted that this predetermined flow of NO is generally adjusted so as to be small to prevent injuries to the patient.

In a most simple embodiment, the valve portion 137 is a normally open valve that is configured manually and that is kept closed by a power signal coming from the control unit 102 via the data cable 141 and the valve actuating portion 139. If the control circuit 102 fails so that the power signal is no longer present, for example if the electrical power fails, the valve portion 137 reverts to its normally open state. Of course, other types of detection are possible to determine failure of the other elements of the injection system 100.

A monitoring unit 161 may also be connected to a monitoring aperture 163 via a conduit 165 when monitoring is necessary. It is to be noted that continuous monitoring is not believed required for the injection system of the present invention. However, monitoring at the beginning of the injection of NO is advantageous since the user may verify that the concentration of NO injected, as determined by the monitoring unit 161, is equal to the concentration of NO displayed on the user interface unit 101.

In operation, when the control unit 102 determines, with the inspiratory gas flow data supplied by either the flowmeter 106 or the ventilator 108, that the patient enters an inspiratory phase, it generates a control signal, supplied to the valve assembly 104 via the control cable 146, to cause the opening of the valve assembly 104 that will allow NO to be transferred from the container 120 to the respiratory system of the patient's through the conduits 114, 150, 152, 118 and endotracheal tube 128. The opening of the valve assembly 104 is variable and is, in a first mode, a function of the inspiratory gas flow data supplied to the control unit 102. Therefore, the concentration of NO injected to the patient during the inspiratory phase is essentially constant since the opening of the valve assembly 104 is proportional to the inspiratory gas flow detected. As will be described hereinafter with reference to FIGS. 11–14, the concentration of injected NO could be non linear with respect to time.

Figure 15:
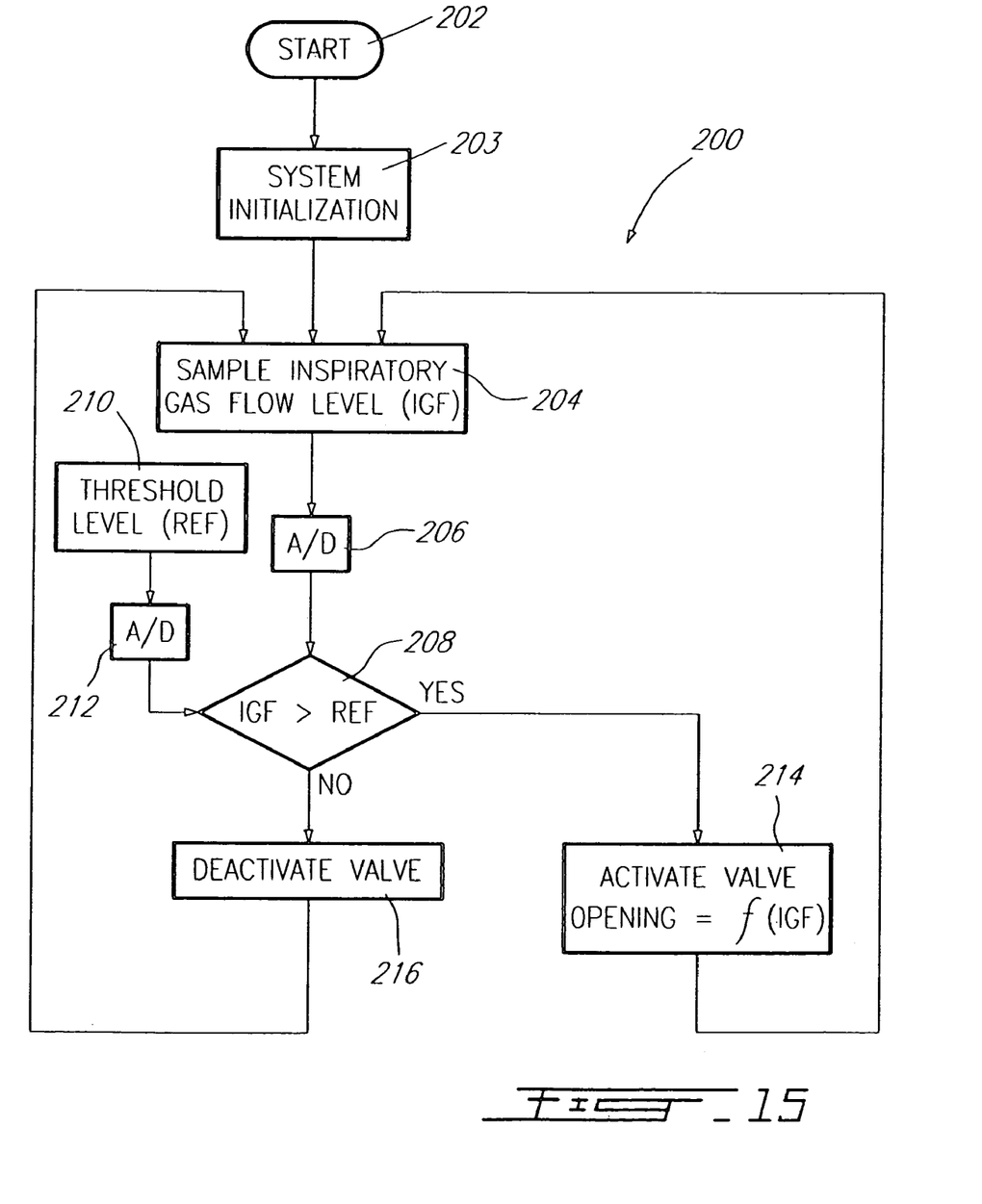
FIG. 15 is a block diagram showing the simplified operation of the injection system of FIG. 5.

Turning now to FIG. 15, of the appended drawings, a simplified block diagram 200 of the operation of the injection system will be described. When the system is started (step 202) it is initialized (step 203). A sample of the inspiratory gas flow (IGF) is then taken (step 204), and is converted to a digital value (step 206) before being supplied to a comparator (step 208). The threshold level (REF, step 210 and numeral 26 in FIG. 5) is also converted to a digital value (step 212) before being supplied to the comparator of step 208.

The comparator then compares IGF and REF to determine if the inspiratory gas flow is greater than the threshold. If so, the valve assembly 104 is activated (step 214) and the opening of the valve 160 by the valve actuating portion 162 is a function of the inspiratory gas flow level (IGF). If not, the valve 160 is deactivated. Of course, as will be described hereinafter, the opening of the valve 160 may be non linear.

Figure 6:
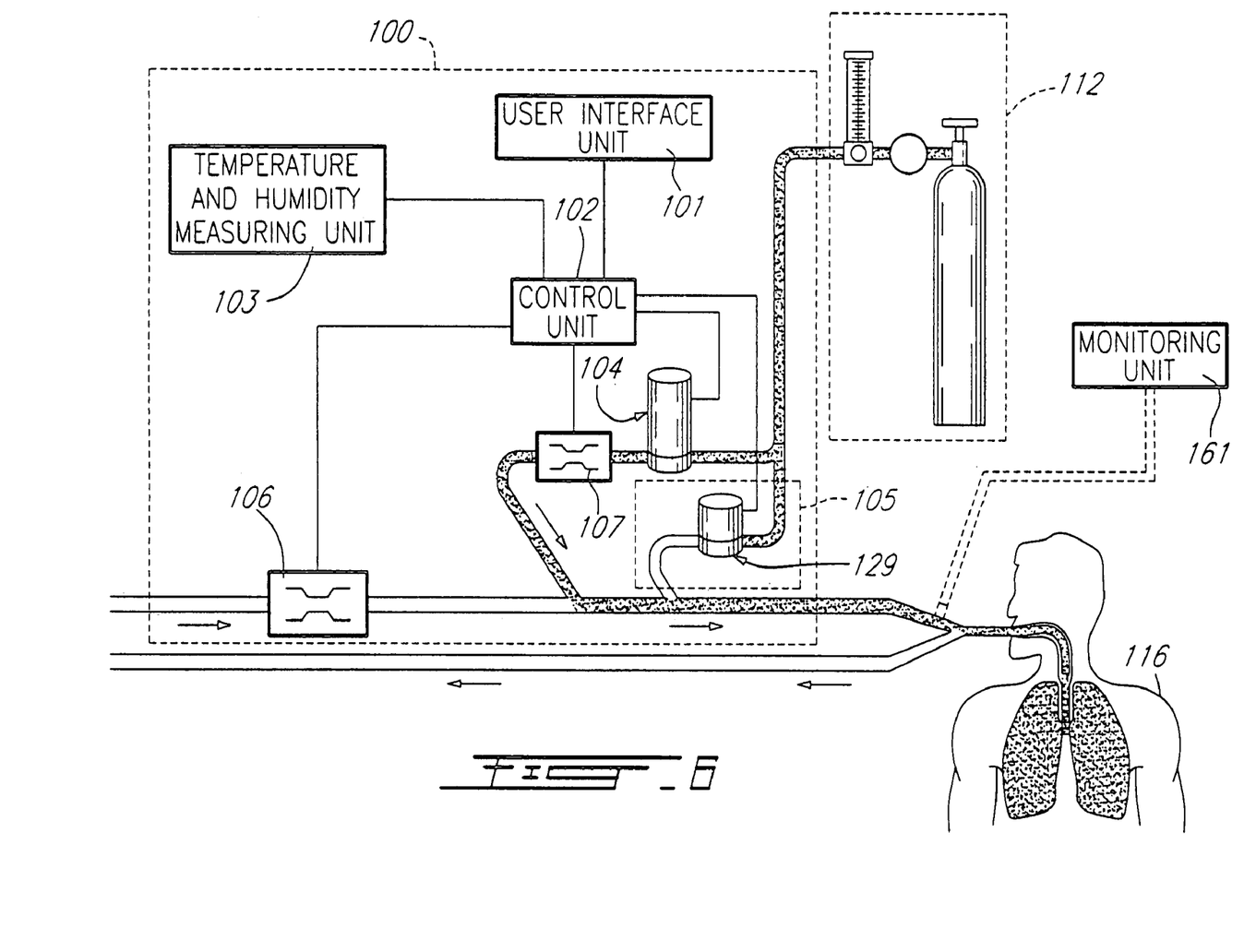
FIG. 6 schematically illustrates the injection system of FIG. 5 when the injection system is not connected to a ventilator.

FIG. 6 of the appended drawings illustrates the injection system 100 used without a ventilator. The only major difference in the operation of the injection system 100 when used without a ventilator is that the inspiratory gas flow data is supplied to the control unit by the flowmeter 106 since the ventilator 108 is not present.

This is a major advantage to be able to use the injection system 100 without a ventilator since the injection of NO may be continued even though the patient 116 does not require a ventilator. The use of the injection system 100 without a ventilator is possible, without danger to the patient, because of the proportional opening of the valve according to the inspiratory gas flow level. Indeed, even if the patient draws short breaths, the concentration of NO with be essentially constant during the inspiratory phases.

Figure 7:
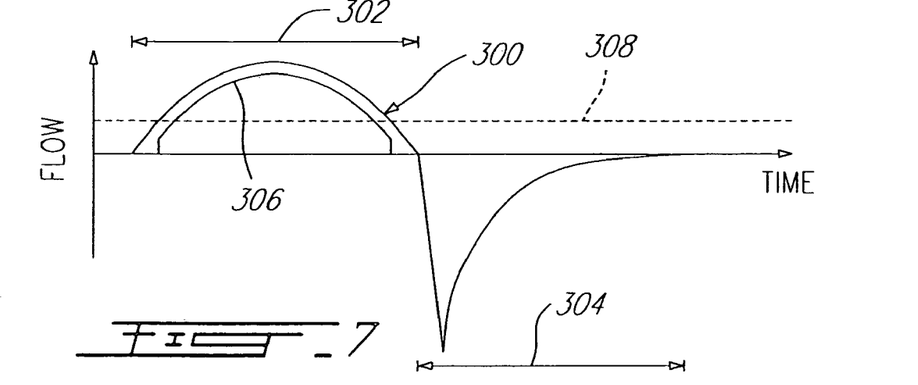
FIG. 7, illustrates a graph of flow vs time for a injection system according to the present invention, the inspiratory phase illustrated could represent a long inspiration.

FIG. 7 of the appended drawings is a graph schematically illustrating the flow 300 vs time for unassisted respiration by a patient. During the inspiratory phase 302 the inspiratory gas flow rise and falls to form a semi-sinusoidal curve. The patient then expires (see expiratory phase 304). When the injection system 100, as illustrated in FIG. 6, is used to inject NO to the patient during the inspiratory phase 302, the flow 306 of NO will begin when the inspiratory gas flow reaches a predetermined threshold 308. The rate of NO injection will then follow the inspiratory gas flow. When the inspiratory gas flow falls below the threshold level 308, the flow of NO is stopped. It is to be noted that the scale is different for the inspiratory gas flow and the flow 306 of NO. Indeed, line 306 illustrating the flow of NO is shown scaled up for illustrative purposes.

Figure 8:
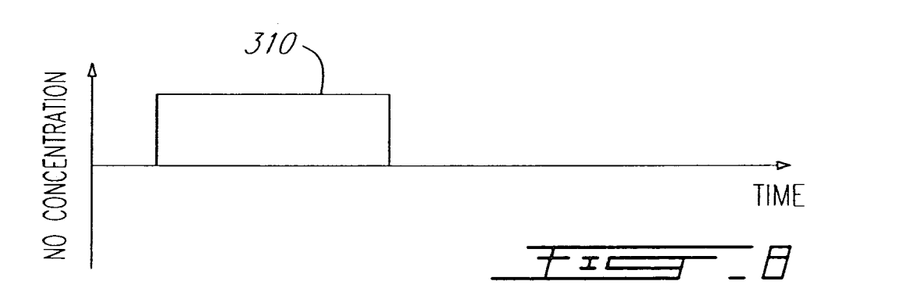
FIG. 8 illustrates a graph of nitric oxide concentration vs time corresponding to the graph of FIG. 7.

As can be seen from FIG. 8, that schematically illustrates the NO concentration 310 vs time, the concentration of NO is constant during the patient's inspiratory phase.

Figure 9:
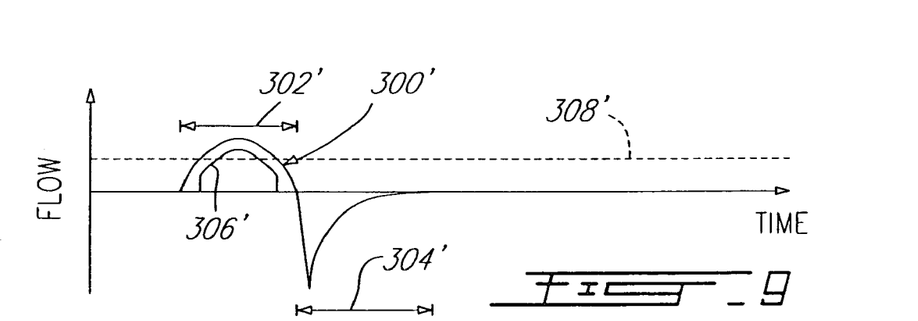
FIG. 9, illustrates a graph of flow vs time for a injection system according to the present invention, the inspiratory phase illustrated could represent a short inspiration.
Figure 10:
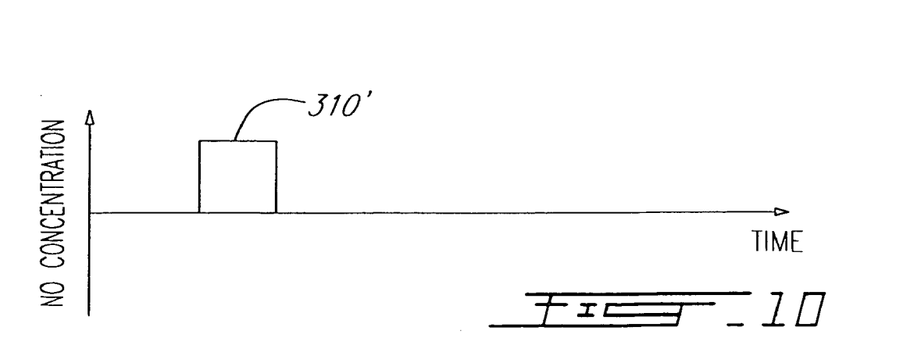
FIG. 10 illustrates a graph of nitric oxide concentration vs time corresponding to the graph of FIG. 9.

FIGS. 9 and 10 are respectively similar to FIGS. 7 and 8 but illustrate a patient taking a relatively short inspiration. As can be seen from FIG. 10, a resulting NO concentration 310' is essentially equal to the NO concentration 310 of FIG. 8. Indeed, with the proportional opening of the valve injecting the NO, changes in the inspiratory gas flow does not modify the injected NO concentration.

As will be readily apparent to one skilled in the art, the inspiratory gas supplied to the patient during the beginning of the inspiratory phase will reach the alveola of the patient, and the inspiratory gas supplied to the patient during the end of the inspiratory phase will stay in the trachea and bronchial tree.

Figure 11:
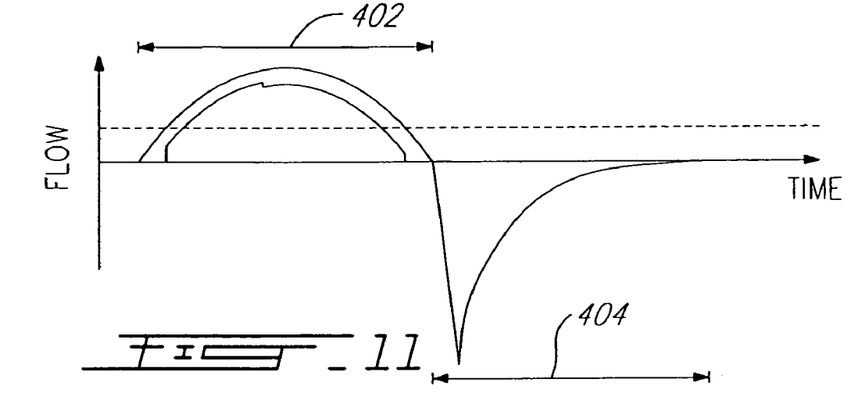
FIG. 11 illustrates a graph of flow vs time for a injection system according to the present invention, the inspiratory phase illustrated generally representing a long inspiration, the flow of injected gaseous substance being modified during the same inspiration.
Figure 12:
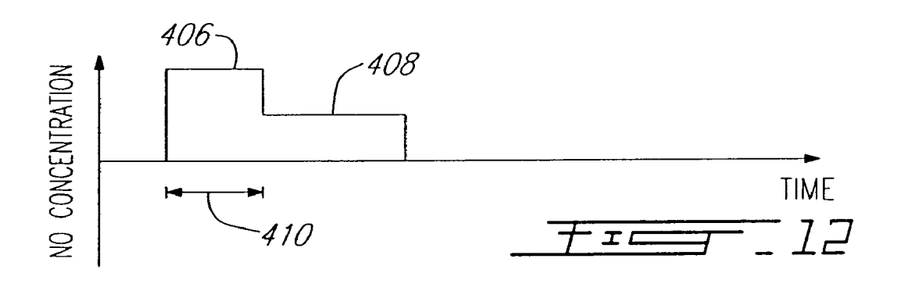
FIG. 12 illustrates a graph of nitric oxide concentration vs time corresponding to the graph of FIG. 11.

FIGS. 11 and 12 illustrate the operation of the injection system of FIG. 5 or 6 when the opening of the valve assembly 104 is not linear but varies in time to deliver a higher concentration 406 of NO during the beginning of the inspiratory phase 402 and to decrease the concentration of NO (see line 408) after a predetermined and programmable time period 410. Indeed, as described hereinabove, the user interface unit 101 includes controls to determine the shape on the NO concentration during each inspiratory phase.

The NO flow pattern illustrated in FIG. 12 could be beneficial to a patient who requires a larger concentration of NO in his alveola than in his bronchial tree.

Figure 13:
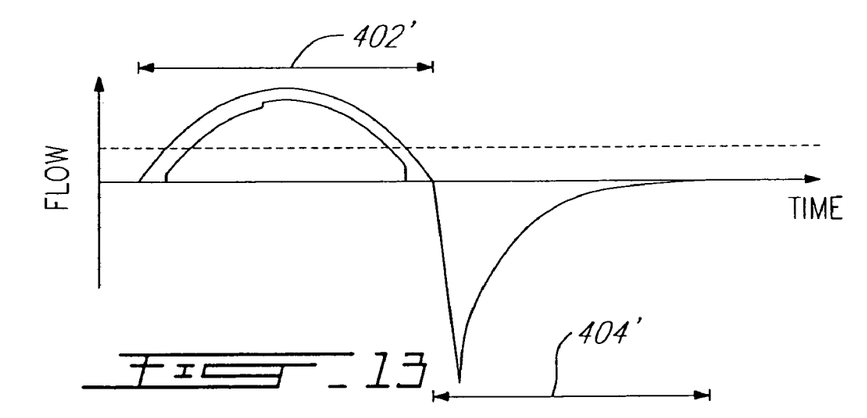
FIG. 13, illustrates a graph of flow vs time for a injection system according to the present invention, the inspiratory phase illustrated generally representing a long inspiration, the flow of injected gaseous substance being modified during the same inspiration.
Figure 14:
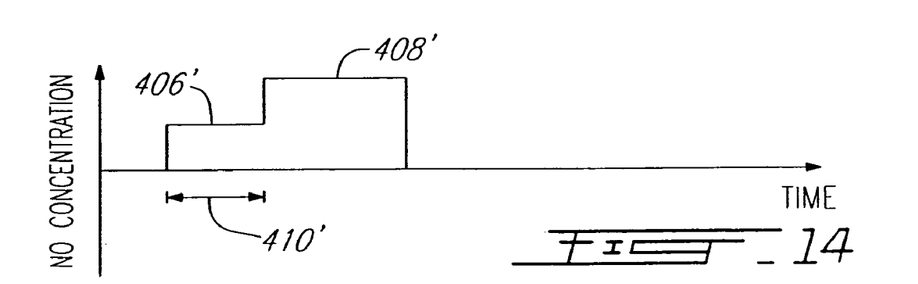
FIG. 14 illustrates a graph of nitric oxide concentration vs time corresponding to the graph of FIG. 13.

Similarly, FIGS. 13 and 14 illustrate the operation of the injection system of FIG. 5 or 6 when the opening of the valve assembly 104 is not linear but varies in time to deliver a lower concentration 406' of NO during the beginning of the inspiratory phase 402' and to increase the concentration of NO (see line 408') after a predetermined and programmable time period 410'. Again, as described hereinabove, the user interface unit 101 includes controls to determine the shape on the NO concentration during each inspiratory phase.

The NO flow pattern illustrated in FIG. 14 could be beneficial to a patient who requires a larger concentration of NO in his bronchial tree than in his alveola.

One skilled in the art will easily be able to modify the configuration of the control unit 102 to achieve the NO concentrations of FIG. 12 or 14, or of any other suitable NO concentration.

Figure 17:
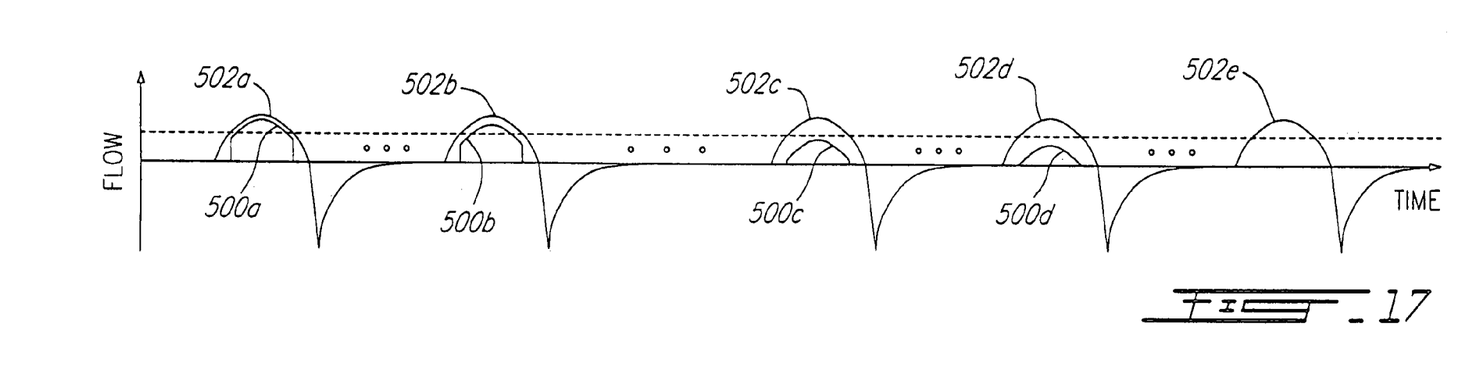
FIG. 17 illustrates a graph of flow vs time for a injection system according to the present invention, the inspiratory phases illustrated generally representing long inspirations, the flow of injected gaseous substance being modified between consecutive inspirations.
Figure 18:
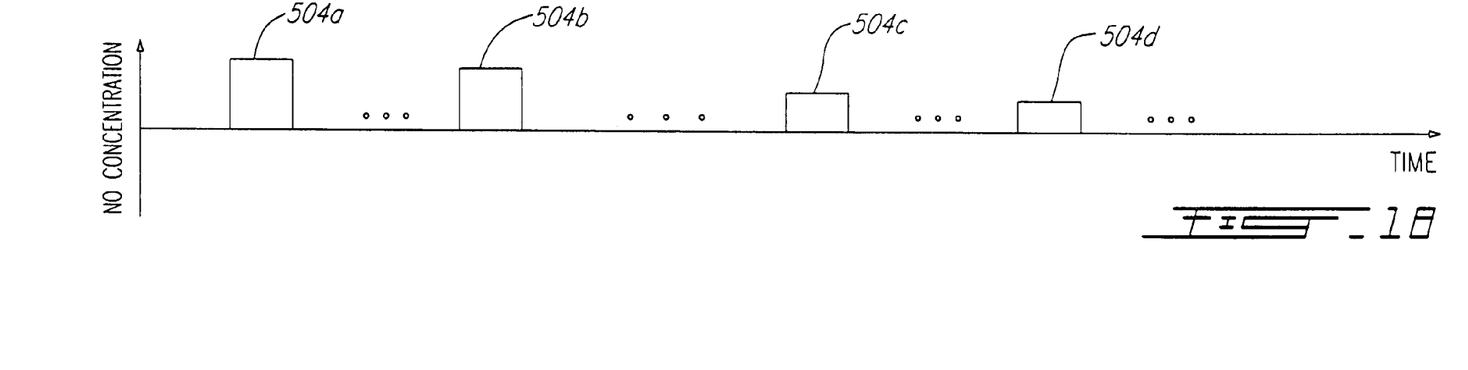
FIG. 18 illustrates a graph of nitric oxide concentration vs time corresponding to the graph of FIG. 17.

Turning now briefly to FIGS. 17 and 18, the control unit 102 may also be configured, via the user interface unit 101, to progressively decrease the NO concentration injected to the patient over a predetermined number of injection phases or over a predetermined time. The flow of NO (500a–500d in FIG. 17) is thus decreased of a minute amount at each inspiratory phase 502a–502e to yield decreasing NO concentrations 504a–504d in FIG. 18. Of course, many inspiratory phases (not shown) are taken by the patient between adjacent inspiratory phases illustrated.

Figure 19:
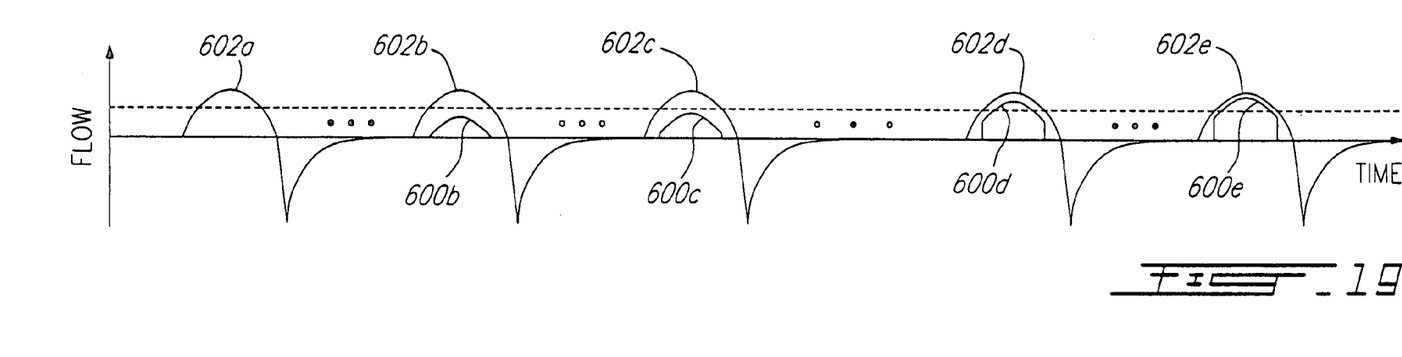
FIG. 19 illustrates a graph of flow vs time for a injection system according to the present invention, the inspiratory phases illustrated generally representing long inspirations, the flow of injected gaseous substance being modified between consecutive inspirations.
Figure 20:
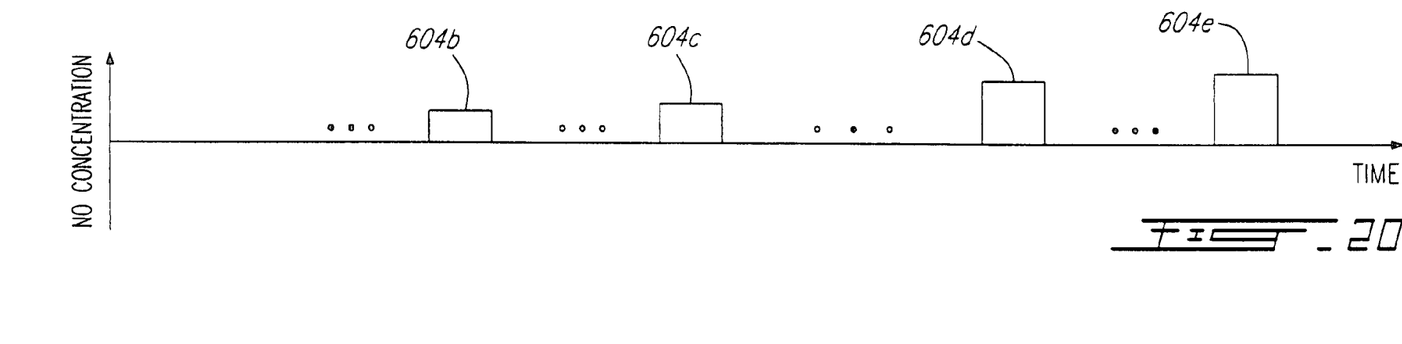
FIG. 20 illustrates a graph of nitric oxide concentration vs time corresponding to the graph of FIG. 19.

Turning now briefly to FIGS. 19 and 20, the control unit 102 may also be configured, via the user interface unit 101, to progressively increase the NO concentration injected to the patient over a predetermined number of injection phases or over a predetermined time. The flow of NO (600b–600e in FIG. 19) is thus increased of a minute amount at each inspiratory phase 602a–602e to yield decreasing NO concentrations 604b–604e in FIG. 20. Of course, many inspiratory phases (not shown) are taken by the patient between adjacent inspiratory phases illustrated.

Figure 16:
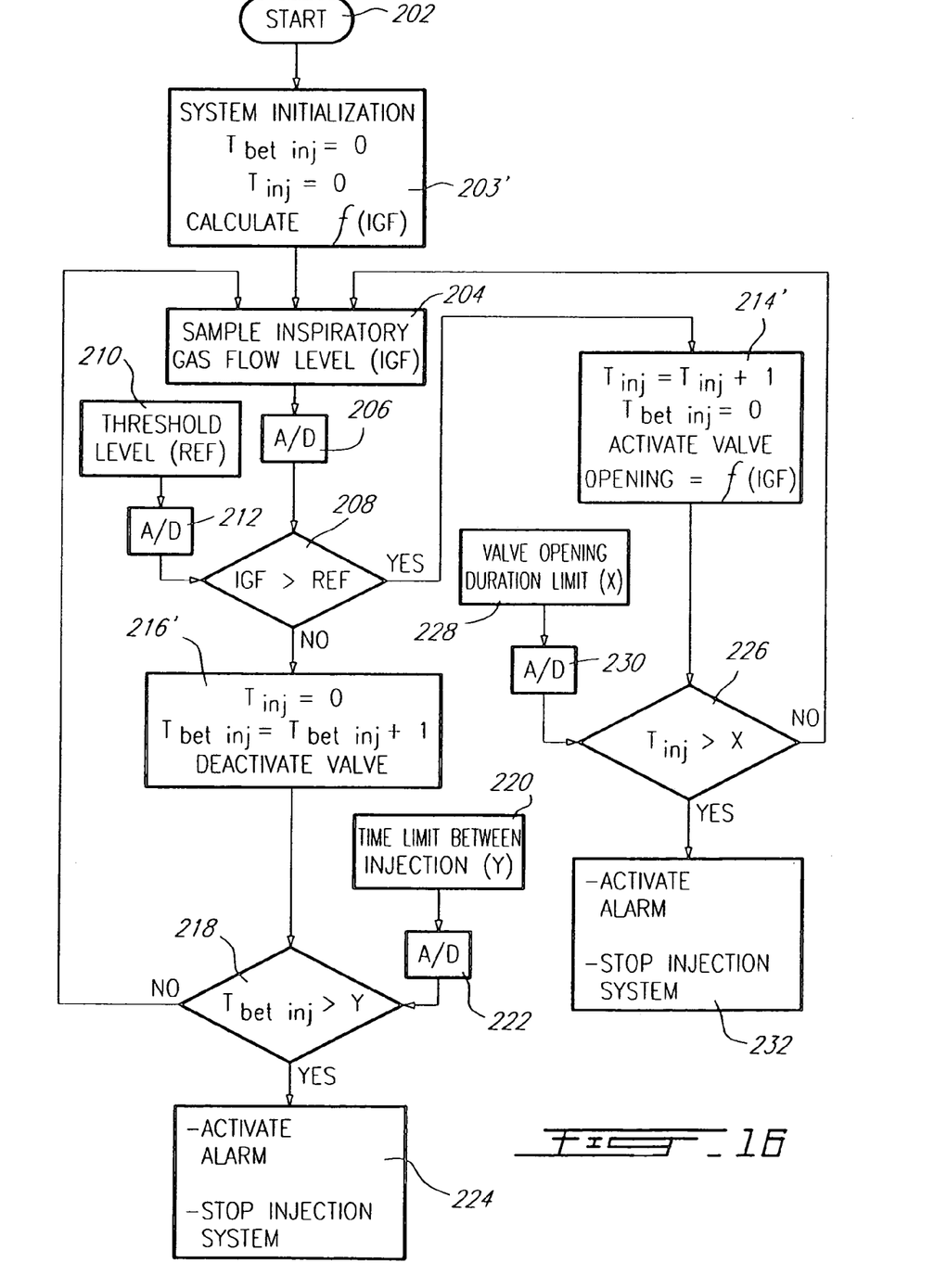
FIG. 16 is a block diagram showing the operation of the injection system of FIG. 5, including safety features.

FIG. 16 is a block diagram illustrating an other mode of operation of the injection system 100. It is to be noted that the mode of operation of FIG. 16 could be used when the injection system 100 is used in conjunction with a ventilator 108 (see FIG. 5). However, this mode of operation is advantageously used when the injection system 100 is used without a ventilator as can be seen in FIG. 6.

The mode of operation of FIG. 16 is similar to the mode of operation of FIG. 15. The extra steps, described hereinafter, are taken to provide safe operation of the injection system 100.

In step 216', a first variable ($T_{inj}$), representing the duration of an injection, is reset and a second variable ($T_{bet\ inj}$), representing the duration between injection, in incremented. The formula f(IGF) representing the opening variations of the valve over time is determined using the data supplied by the user via the user interface unit 101 and other data of the system such as, for example, temperature and humidity data supplied by the measuring unit 103.

Then, in step 218, the second variable $T_{bet\ inj}$ is compared to a predetermined reference number (Y, steps 220 and 222) to activate an alarm and stop the injection system (step 224) should $T_{bet\ inj}$ be greater than Y. This alarm would indicate that there is a condition preventing the normal injection of NO and that supervision is required.

Similarly, in step 214', $T_{inj}$ is incremented and $T_{bet\ inj}$ is reset. Then, in step 226, the second variable $T_{inj}$ is compared to a predetermined reference number (X, steps 228 and 230) to activate an alarm and stop the injection system (step 232) should $T_{inj}$ be greater than X. This alarm would indicate that a malfunction exists in the injection system and that the valve is continuously open.

Of course, the analog to digital conversion steps 206, 212, 222 and 230 could be omitted if the data is already in a digital format.

As will be apparent to one of ordinary skill in the art, the variable opening of the valve assembly 104 is not essentially proportional to the inspiratory gas flow supplied to the patient. Indeed, the opening could be responsive to the inspiratory gas flow in any other suitable manner.

It is to be noted that the concentration of NO and of $NO_2$ (or of any other gaseous substance injected and their derivative) could be monitored downstream from the "Y" junction 153 by using an appropriate monitoring system 161 for the gaseous substance injected.

It is also to be noted that any adequate flowmeter may be used for the flowmeter 106. However, it has been found advantageous to use a pneumotachometer (PNT) since it is already used in medical application, many models are available through different makers, it is approved by the Food & Drug Administration (FDA), it is sufficiently accurate and is reasonably priced, it is known to users and its performances are well documented since it has been used for years. It is however to be noted that PNT usually do not indicate the mass flow of fluid. As will be apparent to one skilled in the art, the control unit 102 may calculate the mass flow of the inspiratory gas and of the NO since it is supplied with the composition of these gases (via the user interface unit 101) and it is supplied with the temperature and relative humidity of the injection system 100 (via the temperature and humidity measuring unit 103).

As it will be easily understood by one skilled in the art, by installing the PNT inside the injection system 100 it is possible to control the condensation on the PNT to prevent a dramatic decrease in precision.

As will be readily apparent to one skilled in the art, the control unit 102 could include an electronic circuit, a programmable micro controller and/or a microprocessor, to control the operation of the injection system 100.

Although the present invention has been described hereinabove by way of preferred embodiments thereof, it can be modified, without departing from the spirit and nature of the subject invention as defined in the appended claims.

What is claimed is:

1. An injection system for the delivery of a gaseous substance from a container to a patient through a conduit coupled to the patient's respiratory system; said injection system comprising:
   a control unit controlling said injection system;
   a valve assembly in connection with the conduit to selectively allow the delivery of the gaseous substance from the container to the conduit; said valve assembly including a valve and valve actuating means allowing variable opening of said valve; said valve actuating means being coupled to said control unit to be controlled thereby; and
   a flowmeter quantitatively measuring inspiratory gas flow in the conduit; said flowmeter being coupled to said control unit to supply inspiratory gas flow data thereto; wherein a) said control unit controls unit is so configured as to receive and analyse said inspiratory gas flow data and as to control said valve assembly so that said variable opening of said valve is responsive to said inspiratory gas flow in the conduit so as to achieve a predetermined concentration of the gaseous substance with respect to the inspiratory gas, b) said control unit is so configured as to vary said predetermined concentration within a plurality of inspiratory phases of the patient on the basis of said inspiratory gas flow data, and said control unit opens said valve in response to said inspiratory gas flow when said inspiratory gas flow exceeds a predetermined threshold level; said injection system therefore delivering the gaseous substance only when the patient is in an inspiratory phase and said control unit includes an alarm actuated when a duration of an inspiratory phase exceeds a predetermined duration limit.

2. An injection system as recited in claim 1, wherein said variable opening of said valve is proportionally responsive to said inspiratory gas flow in the conduit.

3. An injection system as recited in claim 1, wherein said control unit includes an alarm actuated when a duration between two consecutive inspiratory phases exceeds a predetermined duration limit.

4. An injection system as recited in claim 3, wherein said injection system is deactivated when said alarm is actuated.

5. An injection system as recited in claim 1, wherein said controlling unit includes a user interface unit configured to receive inputs from a user and to display data to the user.

6. An injection system as recited in claim 1, wherein said gaseous substance includes nitric oxide.

7. An injection system for the delivery of a gaseous substance from a container to a patient through a conduit mountable to the patient's pulmonary respiratory system along with a ventilator also mountable to the patient's pulmonary respiratory system for forcing inspiratory gas therein; said injection system comprising:
   a control unit controlling said injection system; said control unit being so configured as to receive and analyse inspiratory gas flow data from the ventilator; and
   a valve assembly in connection with the conduit to selectively allow the delivery of the gaseous substance from the container to the conduit; said valve assembly including a valve and valve actuating means allowing variable opening of said valve; said valve actuating means being coupled to said control unit to be controlled thereby;

wherein a) said control unit is so configures as to control said valve assembly so that said variable opening of said valve is responsive to said inspiratory gas flow supplied to the patient so as to achieve a predetermined concentration of the gaseous substance with respect to the inspiratory gas, b) said control unit is so configured as to vary said predetermined concentration within a plurality of inspiratory phases of the patient on the basis of said inspiratory gas flow data, and said control unit opens said valve in response to said inspiratory gas flow when said inspiratory gas flow exceeds a predetermined threshold level; said injection system therefore delivering the gaseous substance only when the patient is in an inspiratory phase and said control unit includes an alarm actuated when a duration of an inspiratory phase exceeds a predetermined duration limit.

8. An injection system as recited in claim 7, wherein said variable opening of said valve is proportionally responsive to said inspiratory gas flow forced by the ventilator in the respiratory system of the patient.

9. An injection system as recited in claim 7, wherein said control unit includes an alarm actuated when a duration between two consecutive inspiratory phases exceeds a predetermined duration limit.

10. An injection system as recited in claim 9, wherein said injection system is deactivated when said alarm is actuated.

11. An injection system as recited in claim 7, wherein said controlling unit includes a user interface unit configured to receive inputs from a user and to display data to the user.

12. An injection system as recited in claim 7, wherein said gaseous substance includes nitric oxide.

* * * * *